United States Patent
Gilbert

(10) Patent No.: US 11,135,002 B2
(45) Date of Patent: Oct. 5, 2021

(54) SYSTEM AND METHOD FOR TEMPERATURE ENHANCED IRREVERSIBLE ELECTROPORATION

(71) Applicant: COVIDIEN LP, Mansfield, MA (US)

(72) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 438 days.

(21) Appl. No.: 16/258,823

(22) Filed: Jan. 28, 2019

(65) Prior Publication Data

US 2019/0151008 A1 May 23, 2019

Related U.S. Application Data

(62) Division of application No. 15/161,400, filed on May 23, 2016, now Pat. No. 10,188,449.

(51) Int. Cl.
*A61B 18/00* (2006.01)
*A61B 18/12* (2006.01)
*A61B 18/14* (2006.01)

(52) U.S. Cl.
CPC ...... *A61B 18/1206* (2013.01); *A61B 18/1492* (2013.01); *A61B 2018/00577* (2013.01); *A61B 2018/00613* (2013.01); *A61B 2018/00642* (2013.01); *A61B 2018/00702* (2013.01); *A61B 2018/00732* (2013.01); *A61B 2018/00773* (2013.01); *A61B 2018/00779* (2013.01); *A61B 2018/126* (2013.01); *A61B 2018/128* (2013.01); *A61B 2018/1253* (2013.01); *A61B 2018/1266* (2013.01); *A61B 2018/1286* (2013.01)

(58) Field of Classification Search
CPC .......... A61B 18/1206; A61B 2018/126; A61B 2018/1266; A61B 2018/1273; A61B 2018/00613; A61N 1/0412–0448; A61N 1/327

See application file for complete search history.

(56) References Cited

U.S. PATENT DOCUMENTS 6,485,961 B1 * 11/2002 Meserol ............... A61N 1/0412
204/290.12
2004/0236376 A1 * 11/2004 Miklavcic ............. A61N 1/325
607/3

(Continued)

FOREIGN PATENT DOCUMENTS

EP 2425871 A2 3/2012
EP 2777578 A1 9/2014
WO 2012088149 A2 6/2012

OTHER PUBLICATIONS

European Examination Report dated Aug. 31, 2020 issued in corresponding EP Appln. No. 17172131.9.

(Continued)

*Primary Examiner* — Jaymi E Della
(74) *Attorney, Agent, or Firm* — Carter, DeLuca & Farrell LLP

(57) ABSTRACT

An electrosurgical generator is disclosed. The electrosurgical generator includes: a power supply configured to output DC power; an inverter coupled to the power supply, the inverter including a plurality of switching elements; and a controller coupled to the inverter and configured to signal the inverter to simultaneously generate based on the DC power a radio frequency heating waveform and an electroporation waveform.

7 Claims, 3 Drawing Sheets

(56) References Cited

U.S. PATENT DOCUMENTS

| | | |
|---|---|---|
| 2005/0004564 A1 | 1/2005 | Wham et al. |
| 2009/0076502 A1 | 3/2009 | Azure |
| 2010/0023004 A1* | 1/2010 | Francischelli ..... A61B 18/1442 606/41 |
| 2011/0028963 A1 | 2/2011 | Gilbert |
| 2011/0054460 A1 | 3/2011 | Gilbert |
| 2011/0112520 A1 | 5/2011 | Michael |
| 2011/0115562 A1 | 5/2011 | Gilbert |
| 2011/0160514 A1 | 6/2011 | Long |
| 2011/0193608 A1 | 8/2011 | Krapohl |
| 2011/0218526 A1 | 9/2011 | Mathur |
| 2011/0224663 A1 | 9/2011 | Heim et al. |
| 2012/0109122 A1* | 5/2012 | Arena ................... A61B 18/14 606/41 |
| 2012/0215216 A1 | 8/2012 | Friedrichs et al. |
| 2014/0066913 A1* | 3/2014 | Sherman ............ A61B 18/1492 606/20 |
| 2014/0254221 A1 | 9/2014 | Johnson et al. |
| 2015/0025523 A1 | 1/2015 | Friedrichs et al. |
| 2015/0088117 A1 | 3/2015 | Gilbert et al. |
| 2016/0074626 A1 | 3/2016 | Weadock et al. |
| 2017/0128126 A1 | 5/2017 | Sunenshine |

OTHER PUBLICATIONS

European Search Report dated Oct. 17, 2017 issued in corresponding European Application No. 17172131.9.

* cited by examiner

SYSTEM AND METHOD FOR TEMPERATURE ENHANCED IRREVERSIBLE ELECTROPORATION

CROSS-REFERENCE TO RELATED APPLICATION

The present application is a divisional of U.S. patent application Ser. No. 15/161,400, filed May 23, 2016, now U.S. Pat. No. 10,188,449 the entire disclosure of which is incorporated by reference herein.

BACKGROUND

Technical Field

The present disclosure relates to systems and methods for electroporation. In particular, the present disclosure relates to an electrosurgical system including a generator configured to generate an electroporation waveform and a radio frequency ("RF") heating waveform.

Background of Related Art

Electrosurgery involves application of high RF electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like.

Another electrosurgical technique is irreversible electroporation (IRE) in which electrical pulses are applied across the tissue cells to generate a destabilizing electric field across cells' outer membrane and cause the formation of permanent nanoscale defects in the lipid bilayer of the cells. The permanent permeabilization of the cell membrane leads to changes in cell homeostasis and results in cell death. This allows IRE to ablate substantial volumes of tissue without the adverse thermal effects of conventional monopolar or bipolar electrosurgical procedures. Thus, there is a need to make IRE even more effective in ablating tissue.

SUMMARY

The present disclosure provides an electrosurgical generator including a non-resonant power converter having one or more switching elements controlled by a switching waveform (e.g., a pulse-width modulated waveform) generated by a controller. The switching waveform is configured to generate two waveforms: an irreversible electroporation ("IRE") waveform and an RF heating form. The power converter is configured to intermix two waveforms to deliver the two waveforms simultaneously or substantially simultaneously to the tissue. The IRE waveform is a pulsatile direct current waveform and is configured to generate an electrical field sufficient to porate cellular membranes. The electroporation waveform includes an initial pulse having a higher peak voltage and a higher rate of increase of voltage over time (dV/dt) than those of subsequent pulses. The heating RF waveform may be a sinusoidal RF waveform configured to heat tissue to a temperature from about 40° C. to about 50° C. Subjecting the tissue to heating during IRE increases effectiveness of the IRE waveform.

According to one embodiment of the present disclosure, an electrosurgical generator is described. The electrosurgical generator includes: a power supply configured to output DC power; an inverter coupled to the power supply, the inverter including a plurality of switching elements; and a controller coupled to the inverter and configured to signal the inverter to simultaneously generate based on the DC power a radio frequency heating waveform and an electroporation waveform.

According to another embodiment of the present disclosure, an electrosurgical system is disclosed. The electrosurgical system includes an electrosurgical generator having: a power supply configured to output DC power; an inverter coupled to the power supply, the inverter including a plurality of switching elements; and a controller coupled to the inverter and configured to signal the inverter to simultaneously generate based on the DC power a radio frequency heating waveform and an electroporation waveform. The electrosurgical system also includes an electrosurgical instrument configured to couple to the inverter and to transmit simultaneously the radio frequency waveform and the electroporation waveform.

According to one aspect of any of the above embodiments, the electroporation waveform is a pulsatile DC waveform configured to generate an electric field and includes a plurality of pulses having an initial pulse with a higher peak voltage and a higher rate of increase of voltage than any subsequent pulse.

According to another aspect of any of the above embodiments, the inverter includes four switching elements arranged in an H-bridge topology.

According to yet another aspect of any of the above embodiments, the radio frequency heating waveform is a sinusoidal waveform and has a fundamental frequency from about 400 kHz to about 600 kHz.

According to a further aspect of any of the above embodiments, the controller is further configured to signal the inverter to generate the radio frequency heating waveform at least one of prior to or following the electroporation waveform.

According to yet another embodiment of the present disclosure, a method for electroporating tissue is described. The method includes: applying a heating radio frequency waveform to tissue through at least one electrode of an electrosurgical instrument; and applying an electroporation waveform to tissue simultaneously with the heating radio frequency waveform through the at least one electrode of the electrosurgical instrument, wherein the electroporation waveform is a pulsatile waveform having a plurality of pulses and an initial pulse with a higher rate of increase of voltage than any subsequent pulse.

According to one aspect of the above embodiment, applying the heating radio frequency waveform includes generating the heating radio frequency waveform having a fundamental frequency from about 400 kHz to about 600 kHz.

According to another aspect of the above embodiment, applying the heating radio frequency waveform includes generating the heating radio frequency waveform having a crest factor of about 1.4.

According to yet another aspect of the above embodiment, the electroporation waveform is a DC waveform.

According to a further aspect of the above embodiment, the heating radio frequency waveform is applied in between each of the plurality of pulses of the electroporation waveform.

According to yet a further aspect of the above embodiment, the heating radio frequency waveform is applied prior to, during, and/or after application of the electroporation waveform.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that the illustrative embodiments of the present disclosure may be adapted for use with any electrosurgical instrument. It should also be appreciated that different electrical and mechanical connections and other considerations from those described in the present disclosure may apply to each particular type of instrument.

Briefly, an electrosurgical system according to the present disclosure includes a generator which can generate an IRE waveform and an RF waveform either simultaneously or intermittently. The generator may be used with any suitable electrosurgical instrument configured to supply the IRE waveform and the RF waveform to tissue.

Figure 1:
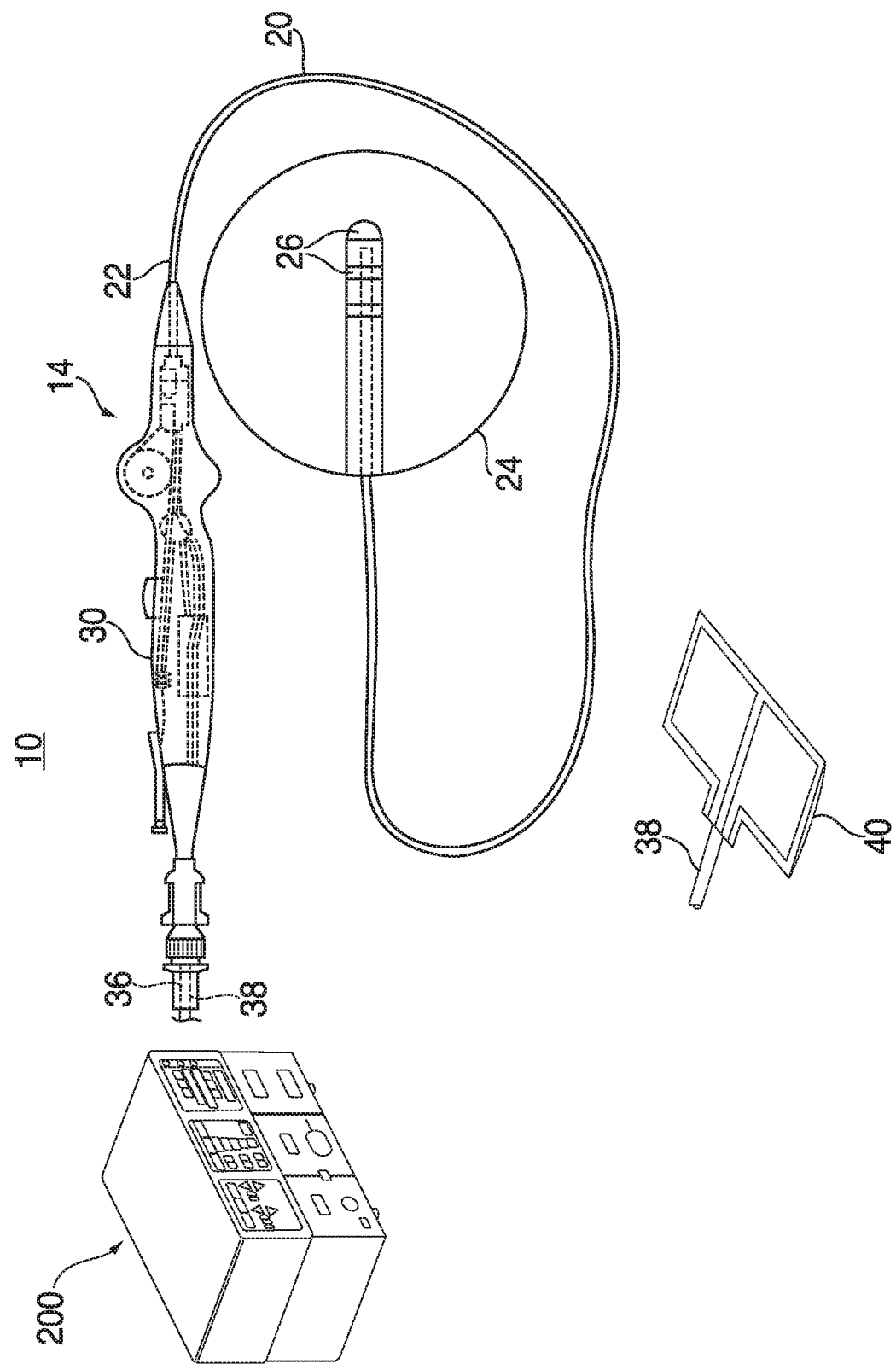
FIG. 1 is a perspective view of an electrosurgical system according to an embodiment of the present disclosure.

Referring to FIG. 1, an electrosurgical system 10 according to the present disclosure includes a generator 200 and one or more electrosurgical instruments 14, such as, an RF ablation catheter. The electrosurgical instrument 14 may be adapted for use with an energy modality that heats tissue including, but not limited to, RF current, light energy, and ultrasonic energy. The electrosurgical instrument 14 is also configured to generate an electric field to electroporate target tissue. The electrosurgical instrument 14 may include a flexible elongate body 20 having a proximal portion 22 and a distal portion 24. The distal portion 24 of the elongate body 20 may have a fixed diameter or may include an expandable element. The elongate body 20 may include a plurality of treatment elements, such as electrodes 26, at the distal portion 24 for delivering energy to target tissue.

The plurality of electrodes 26 may be of any suitable configuration, or shape; for example, a plurality of discrete electrodes, or band electrodes that partially or entirely circumscribe the elongate body 20. The electrodes may be in the form of conductive strips applied to the outer surface of the distal portion 24 of electrosurgical instrument 14, and may be made of metal, conductive polymers, conductive ink, or micro-capillary printed. The electrodes 26 may be secured to the distal portion 24 by any suitable method, such as, for example by being adhesively bonded to the distal portion 24 or applied by ion-deposition or plasma deposition. Alternatively, conductive materials such as silver, platinum, or gold may be doped or otherwise mixed into the material of the elongate body 20.

The proximal portion 22 of the elongate body 20 may be coupled to a handle 30, which may include various ports (not shown) for electrical and fluid connectors, leads, junctions, or tubes, and may also include various control assemblies, such as switches, buttons, or valves, as well as safety detection or shutdown components. The handle 30 may include connectors that are matable directly or indirectly by way of one or more ports of the generator 200 as described in further detail below. Further, the handle 30 may also include an element such as a lever or knob (not shown) for manipulating or deflecting at least a portion of the elongate body 20.

Electrosurgical alternating RF current is supplied to one or more of the electrodes 26 of the electrosurgical instrument 14 by the generator 200 via a supply line 36 that is connected to an active terminal 230 (FIG. 2) of the generator 200. The alternating RF current is returned to the generator via a return line 38 coupled to a return terminal 232 (FIG. 2) of the generator 200 either through one of the other electrodes 26 if the electrosurgical instrument 14 is operated in a bipolar mode or through a return electrode pad 40 if the electrosurgical instrument 14 is operated in a monopolar mode.

The RF current may be supplied to the electrosurgical instrument 14 in any suitable modality including, unipolar, bipolar, or combinations thereof. For monopolar operation, the system 10 may include a plurality of return electrode pads 40 that, in use, are disposed on a patient to provide a return path remote from the active electrode for the current to return to the generator to complete the circuit. In addition, the generator 200 and the return electrode pads 40 may be configured for monitoring tissue-to-patient contact to ensure that sufficient contact exists therebetween for optimal current flow.

Figure 2:
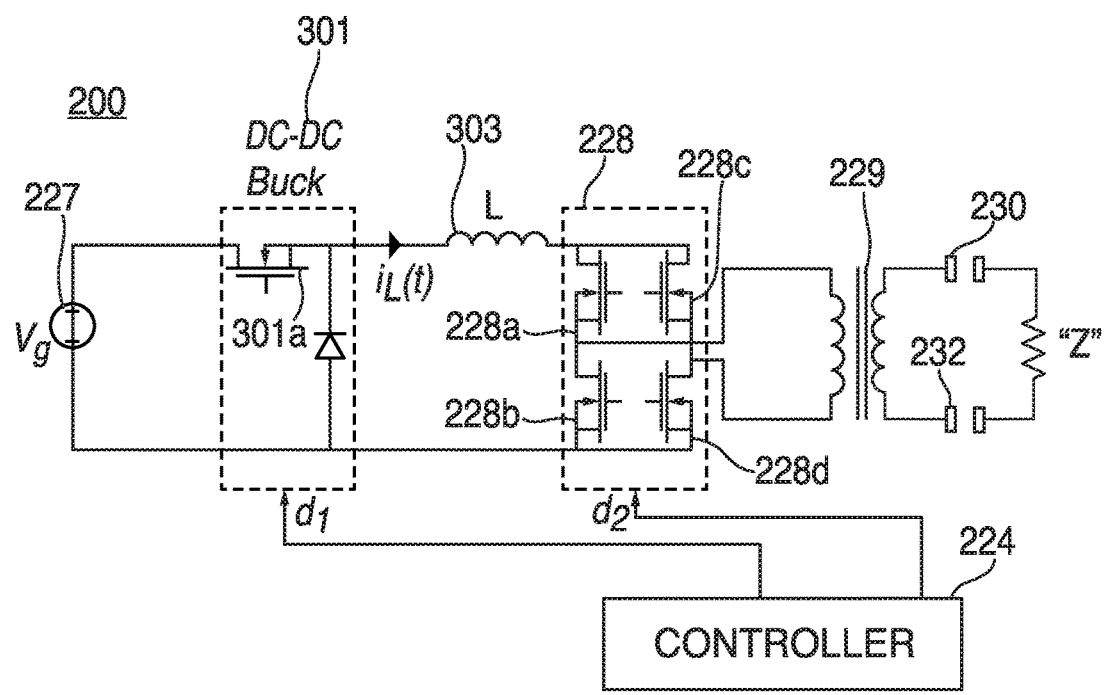
FIG. 2 is a schematic diagram of an electrosurgical generator of the electrosurgical system of FIG. 1 according to an embodiment of the present disclosure.

Referring to FIG. 2 the generator 200 is shown, which includes a controller 224, a power supply 227, and a power converter 228. The power supply 227 may be a high voltage, DC power supply connected to an AC source (e.g., line voltage) and provides high voltage, DC power to the power converter 228, which then converts high voltage, DC power into RF energy and delivers the energy to the active terminal 230. The energy is returned to the generator 200 via the return terminal 232. In particular, electrosurgical energy for energizing the monopolar electrosurgical instrument 14 is delivered through the active and return terminals 230 and 232. The active and return terminals 230 and 232 are coupled to the power converter 228 through an isolation transformer 229.

The generator 200 also includes a DC-DC buck converter 301 coupled to the power supply 227. Furthermore, an inductor 303 is electrically coupled to the DC-DC buck converter 301 and the power converter 228. The inductor 303 may have a relatively large inductance which smoothes the current supplied to the power converter 228. In other words, the inductor 303 is configured to supply relatively constant current to the power converter 228. The output of power converter 228 transmits current through the isolation transformer 229 to the load "Z", e.g., tissue being treated.

The power converter 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Power converter 228 may be a resonant RF amplifier or a non-resonant RF amplifier, as shown. A non-resonant RF amplifier, as used herein, denotes an amplifier lacking any tuning components, i.e., conductors, capacitors, etc., disposed between the power converter and the load "Z."

The controller 224 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 224 includes an output port (not shown) that is operably connected to the power supply 227 and/or power converter 228 allowing the processor to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then controls the power supply 227 and/or power converter 228, which adjusts the DC power and/or RF power, respectively.

The generator 200 according to the present disclosure may also include a plurality of sensors (not shown). The sensors may be coupled to the power supply 227, DC-DC buck converter 301, the inductor 303, and/or power converter 228 and may be configured to sense properties of DC current supplied to the power converter 228 and/or RF energy outputted by the power converter 228, respectively. Various components of the generator 200, namely, the power converter 228, the current and voltage sensors, may be disposed on a printed circuit board (PCB). The controller 224 also receives input signals from the input controls of the generator 200 and the instrument 14. The controller 224 utilizes the input signals to adjust power outputted by the generator 200 and/or performs other control functions thereon.

The DC-DC buck converter 301 includes a switching element 301a and power converter 228 includes a plurality of switching elements 228a-228d arranged in an H-bridge topology. In embodiments, the power converter 228 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicone carbide, or any other suitable wide bandgap materials.

The controller 224 is in communication with switching elements 301a and 228a-228d of the DC-DC buck converter 301 and the power converter 228, respectively. Controller 224 is configured to output control signals, which may be a pulse-width modulated ("PWM") signal, to switching elements 301a and 228a-228d as described in further detail in co-pending application published as U.S. publication no. 2014/0254221, the entire contents of which are incorporated by reference herein. In particular, controller 224 is configured to modulate a control signal $d_1$ supplied to switching element 301a of DC-DC buck converter 301 and control signal $d_2$ supplied to switching elements 228a-228d of power converter 228. Additionally, controller 224 is configured to calculate power characteristics of generator 200, and control generator 200 based at least in part on the measured power characteristics including, but not limited to, current passing through the inductor 303, DC output of the DC-DC buck converter 301, and the voltage and current at the output of power converter 228.

Figure 3:
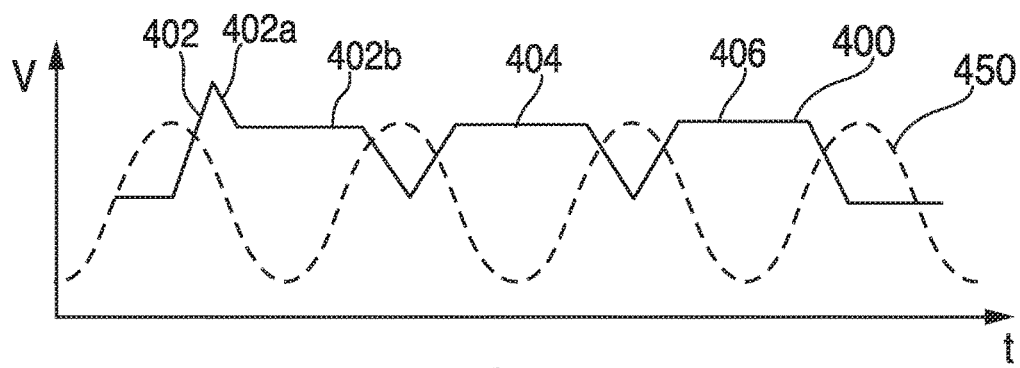
FIG. 3 is a plot of an electroporation waveform and a radio frequency waveform according to one embodiment of the present disclosure.
Figure 4:
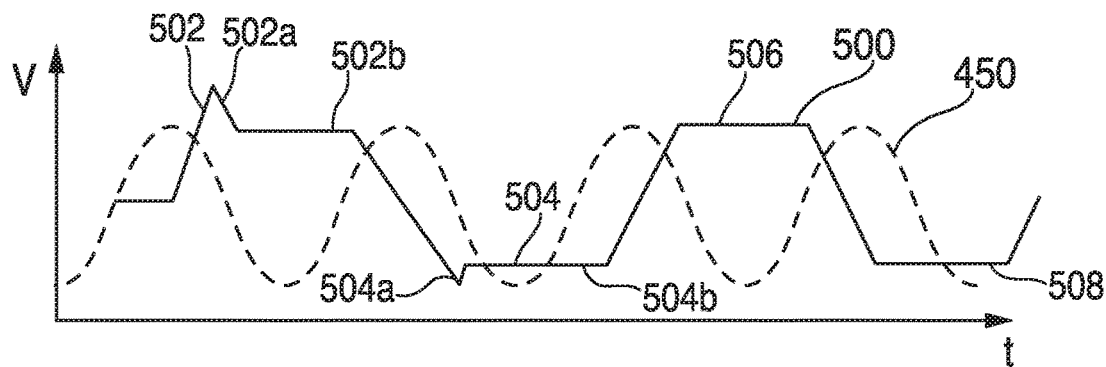
FIG. 4 is a plot of an electroporation waveform and a radio frequency waveform according to another embodiment of the present disclosure.

With reference to FIGS. 3 and 4, the generator 200 according to the present disclosure, and in particular, the controller 224 is configured to operate the power converter 228 to generate simultaneously an IRE waveform 400 (FIG. 3) or an IRE waveform 500 (FIG. 4) 500 along with an RF waveform 450. In embodiments, the IRE waveforms 400, 500 and the RF waveform 450 may be intermixed, such that the RF waveform 450 is supplied in between the pulses 402, 404, and 406 of the IRE waveform 400 and the pulses 502, 504, 506, and 508 of the IRE waveform 500. As shown in FIG. 3, the IRE waveform 500 is monophasic and in FIG. 4, the IRE waveform 500 is biphasic. In particular, in the IRE waveform 400, the pulses 402, 404, and 406 are direct current pulses, whereas the pulses 502, 504, 506, and 508 of the biphasic IRE waveform 500 are alternating current pulses.

The IRE waveform 400 is a pulsatile direct current waveform and includes an initial pulse 402 having a higher peak voltage and a higher rate of increase of voltage over time (dV/dt) than those of subsequent pulses 404 and 406. The pulses may be supplied at a frequency from about 1,000 kHz to about 5,000 kHz, and in in certain embodiments from about 2,000 kHz to about 3,000 kHz. The initial pulse 402 includes a first portion 402a, which increases the voltage of the electric field. The electrical field is then decreased as the initial pulse 402 plateaus at a second, lower, portion 402b. The first portion 402a may be of shorter duration than the second portion 402b, to avoid draining the cells of fluid and other materials via electrophoresis. The first portion 402a also includes the highest peak voltage. The initial pulse 402 increases the voltage of the electric field to a level sufficient to permanently damage the cellular membrane or otherwise form pores therein, i.e., it porates the membrane. Subsequent pulses 404 and 406 generate a pulsatile electric field to continue poration of the cellular membrane.

The IRE waveform 500 is a pulsatile biphasic alternating current waveform and includes an initial pulse 502 having a higher peak voltage and a higher rate of increase of voltage over time (dV/dt) than those of subsequent pulses 504, 506, and 508. The pulses may be supplied at a frequency from about 1,000 kHz to about 5,000 kHz, and in in certain embodiments from about 2,000 kHz to about 3,000 kHz. The initial pulse 502 includes a first portion 502a, which increases the voltage of the electric field. The electrical field is then decreased as the initial pulse 502 plateaus at a second, lower, portion 502b. The first portion 502a may be of shorter duration than the second portion 502b, to avoid draining the cells of fluid and other materials via electrophoresis. The second pulse 504 may also include a first peak portion 504a and a plateau portion 504b. The initial pulses 502 and 504 increases the voltage of the electric field to a level sufficient to permanently damage the cellular membrane or otherwise form pores therein, i.e., it porates the membrane. Subsequent pulses 506 and 508 generate a pulsatile electric field to continue poration of the cellular membrane. The biphasic nature of the IRE waveform 500 reduced muscle stimulation.

The RF waveform 450 is supplied simultaneously with one of the IRE waveform 400 of the IRE waveform 500 through the electrodes 26 of the electrosurgical instrument 14. In embodiments, the RF waveform 450 may be supplied prior to and/or continue after application of the IRE waveforms 400, 500 to pre-heat and/or post-heat the tissue, respectively. The RF waveform 450 may be any suitable RF waveform that heats the tissue when supplied thereto. The RF waveform 450 may be a substantially pure sinusoidal waveform having a crest factor of about 1.4 having a fundamental frequency from about 300 kHz to about 1,000 kHz, and in certain embodiments, from about 400 kHz to about 600 kHz.

Figure 5:
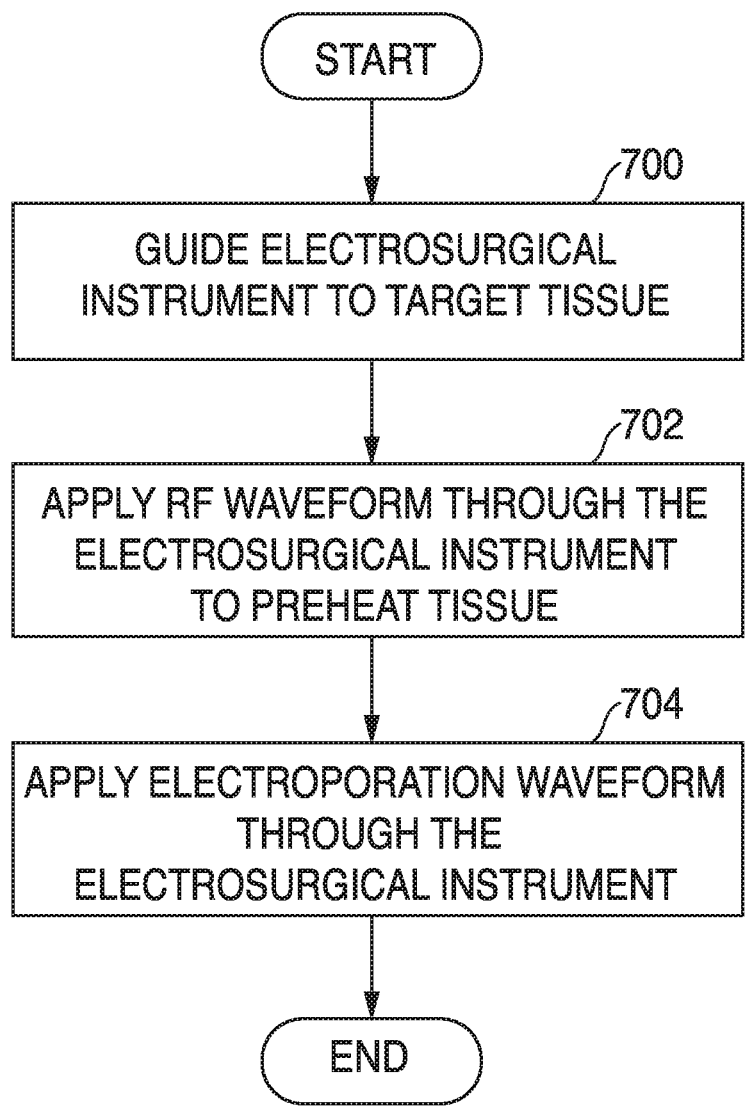
FIG. 5 is a flow chart of a method for electroporating tissue according to an embodiment of the present disclosure.

Referring now to FIG. 5 a method for electroporating tissue begins at step 700, wherein the electrosurgical instrument 14 is guided to a desired target tissue to be electroporated. This may be accomplished using various imaging modalities, such as X-ray, computer aided tomography, positron emission tomography, and the like. In step 702, the RF waveform 450 is supplied to the tissue through the electrosurgical instrument 14 to preheat the tissue to a temperature from about 40° C. to about 55° C., and in certain embodiments the tissue may be preheated to a temperature of from about 45° C. to about 50° C. In further embodiments, tissue may be preheated by any other suitable methods including circulating a heated fluid through the distal portion 24 of the electrosurgical instrument 14, resistive heating, ultrasonic vibrations and the like. In step 704, the IRE waveform 400 is supplied also through the electrosurgical instrument 14 to generate the electrical field for electroporating tissue. The tissue continues to be heated by supplying the RF waveform 450 simultaneously and/or intermittently in between the pulses 402, 404, 406 of the IRE waveform 400 until tissue electroporation is complete. In embodiments, the IRE waveform 400 may be terminated prior to initiating the RF waveform 450, to continue heating the tissue.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for electroporating tissue, the method comprising:
    applying a heating radio frequency waveform to the tissue through at least one electrode of an electrosurgical instrument; and
    applying an electroporation waveform to tissue simultaneously with the heating radio frequency waveform through the at least one electrode of the electrosurgical instrument, wherein the electroporation waveform is a pulsatile waveform having a plurality of pulses and an initial pulse with a higher rate of increase of voltage than any subsequent pulse.

2. The method according to claim 1, wherein applying the heating radio frequency waveform includes generating the heating radio frequency waveform having a fundamental frequency from about 400 kHz to about 600 kHz.

3. The method according to claim 1, wherein applying the heating radio frequency waveform includes generating the heating radio frequency waveform having a crest factor of about 1.4.

4. The method according to claim 1, wherein the electroporation waveform is a direct current (DC) waveform.

5. The method according to claim 1, wherein the heating radio frequency waveform is applied in between each of the plurality of pulses of the electroporation waveform.

6. The method according to claim 1, wherein the heating radio frequency waveform is also applied at least prior to or after application of the electroporation waveform.

7. The method according to claim 1, further comprising:
    generating DC power; and
    inverting the DC power at an inverter to generate the heating radio frequency waveform.

* * * * *